United States Patent
Yu et al.

(10) Patent No.: US 11,800,969 B2
(45) Date of Patent: Oct. 31, 2023

(54) METHOD AND DEVICE FOR MONITORING COLONOSCOPE WITHDRAWAL SPEED

(71) Applicant: Wuhan Endoangel Medical Technology Co., Ltd., Wuhan (CN)

(72) Inventors: Honggang Yu, Wuhan (CN); Bin Liu, Wuhan (CN); Shan Hu, Wuhan (CN); Lianlian Wu, Wuhan (CN)

(73) Assignee: WUHAN ENDOANGEL MEDICAL TECHNOLOGY CO., LTD., Wuhan (CN)

(*) Notice: Subject to any disclaimer, the term of this patent is extended or adjusted under 35 U.S.C. 154(b) by 739 days.

(21) Appl. No.: 16/986,232

(22) Filed: Aug. 5, 2020

(65) Prior Publication Data

US 2020/0364880 A1    Nov. 19, 2020

Related U.S. Application Data

(63) Continuation-in-part of application No. PCT/CN2019/106102, filed on Sep. 17, 2019.

(30) Foreign Application Priority Data

Dec. 5, 2018 (CN) .......................... 201811481234.7

(51) Int. Cl.
*A61B 1/00* (2006.01)
*G06T 7/10* (2017.01)
(Continued)

(52) U.S. Cl.
CPC ........ *A61B 1/00009* (2013.01); *G06T 3/4007* (2013.01); *G06T 7/0014* (2013.01);
(Continued)

(58) Field of Classification Search
CPC ..... A61B 1/00009; G06T 7/10; G06T 7/0014; G06T 7/20; G06T 3/4007; G06T 11/60;
(Continued)

(56) References Cited

U.S. PATENT DOCUMENTS

| | | | |
|---|---|---|---|
| 2007/0271226 A1* | 11/2007 | Zhang | G06F 16/58 |
| 2008/0058593 A1* | 3/2008 | Gu | G06T 5/40 |
| | | | 600/109 |
| 2019/0080454 A1* | 3/2019 | Hameed | G01B 11/03 |

FOREIGN PATENT DOCUMENTS

| | | | | |
|---|---|---|---|---|
| CN | 109166615 A | * | 1/2019 | ............. G16H 30/00 |
| CN | 109598716 A | * | 4/2019 | ......... A61B 1/00009 |
| CN | 114529742 A | * | 5/2022 | |

* cited by examiner

*Primary Examiner* — Khai M Nguyen
(74) *Attorney, Agent, or Firm* — MATTHIAS SCHOLL P.C.; Matthias Scholl

(57) ABSTRACT

A method for monitoring a colonoscope withdrawal speed, the method including: 1) acquiring, a real-time video of colonoscopy, decoding the video into images, cropping the images, and zooming-out the images cropped where texture information of the images is retained; 2) converting the images including the texture information to grayscale images; 3) obtaining Hash fingerprints of the images; 4) calculating a Hamming distance between the images; 5) comparing the Hash fingerprints of a current colonoscopy image with n previous colonoscopy images, to obtain an overlapping rate of the current colonoscopy image with any one of the n previous colonoscopy images; 6) calculating a weighted similarity of the images at a point in time t; 7) converting a weighted overlapping rate of the images at the point in time t into a stability coefficient; and 8) calculating a mean stability coefficient of colonoscopy images within a period of time 0-t.

9 Claims, 3 Drawing Sheets

(51) Int. Cl.
*G06T 3/40* (2006.01)
*G06T 7/00* (2017.01)
*G06T 7/20* (2017.01)
*G06T 11/60* (2006.01)

(52) U.S. Cl.
CPC .............. *G06T 7/10* (2017.01); *G06T 7/20* (2013.01); *G06T 11/60* (2013.01); *G06T 2207/10016* (2013.01); *G06T 2207/10068* (2013.01); *G06T 2207/20132* (2013.01); *G06T 2207/30028* (2013.01)

(58) Field of Classification Search
CPC . G06T 2207/10016; G06T 2207/10068; G06T 2207/20132; G06T 2207/30028
See application file for complete search history.

| P2-1 | P20 | P21 | P22 |
| P1-1 | P10 | P11 | P12 |
| P0-1 | P00 | P01 | P02 |
| P-1-1 | P-10 | P-11 | P-12 |

FIG. 3

METHOD AND DEVICE FOR MONITORING COLONOSCOPE WITHDRAWAL SPEED

CROSS-REFERENCE TO RELATED APPLICATIONS

This application is a continuation-in-part of International Patent Application No. PCT/CN2019/106102 with an international filing date of Sep. 17, 2019, designating the United States, now pending, and further claims foreign priority benefits to Chinese Patent Application No. 201811481234.7 filed Dec. 5, 2018. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, MA 02142.

BACKGROUND

The disclosure belongs to the field of information technology, and more particularly relates to a method and device for monitoring a colonoscope withdrawal speed.

Colonoscopy is a common method of screening for lower gastrointestinal lesions such as colorectal polyps and tumors. Colonoscopy withdrawal time refers to the actual time from the insertion of the colonoscope to the cecum to the withdrawal of the colonoscope out of the anal canal, excluding the time taken for maneuvers such as staining or biopsy. Studies have shown that, as the withdrawal time increases, the detection rates of polyps and adenomas, and the average number of polyps found in patients increase significantly. Therefore, the withdrawal time is considered as an important indicator of the quality of colonoscopy, and the guidelines for colonoscopy all over the world recommend a colonoscopy withdrawal time of 6-10 minutes. However, in actual clinical practice, the colonoscope withdrawal speed and time lack of supervision and monitoring.

SUMMARY

The disclosure provides a method for monitoring a colonoscope withdrawal speed, the method comprising:
1) acquiring, by endoscopic equipment, a real-time video of colonoscopy; decoding the video into images, cropping the images, and zooming-out the cropped images to remove the color and leave texture information of the images;
2) converting the images comprising the texture information to grayscale images;
3) obtaining Hash fingerprints of the grayscale images;
4) calculating a Hamming distance between the images;
5) comparing the Hash fingerprints of a current colonoscopy image with n previous colonoscopy images where n is a number, to obtain an overlapping rate of the current colonoscopy image with any one of the n previous colonoscopy images, thereby obtaining a similarity between the current colonoscopy image and the any one of the n previous colonoscopy images;
6) calculating a weighted similarity of the images at a point in time t, wherein the weighted similarity refers to a weighted average value of similarity between a current image and its previous 9 frames, thereby acquiring a representative value of the similarity within the point in time t, and the closer two frames are, the higher the weighted similarity is;
7) converting the weighted similarity of the images at the point in time t into a stability coefficient;
8) calculating a mean stability coefficient of colonoscopy images within a period of time 0-t as follows: the mean stability coefficient=100−weighted similarity, time 0 is a timepoint where the colonoscopy withdrawal process begins, and the time t is any given timepoint;
9) analyzing the real-time video of colonoscopy to obtain a first boundary between a standard colonoscopy video where a withdrawal time exceeds 6 min and a sub-standard colonoscopy video where a withdrawal time is between 5-6 min and a second boundary between the sub-standard colonoscopy video and a low-quality colonoscopy video where a withdrawal time is less than 5 min, respectively; and
10) monitoring in real time, according to the operations 1) to 8), a stability coefficient of a withdrawal process, and feeding back the stability coefficient to an operator, wherein: when the stability coefficient is less than the first boundary, indicating the withdrawal speed of the colonoscopy is within a normal range and the withdrawal speed meets the requirement of standard colonoscopy guideline; when the stability coefficient is greater than the first boundary, indicating the withdrawal speed of the colonoscopy is not within the normal range; when the stability coefficient is between the first boundary and the second boundary, a warning signal is presented in a dashboard monitoring real-time withdrawal speed during colonoscopy; and when the stability coefficient is greater than the second boundary, an emergency alarm is given.

In 1), the cropped images are zoomed-out by bicubic (cubic convolution) interpolation.

In 2), the images are converted to grayscale images by the following equation: Gray=0.30×R+0.59×G+0.11×B, where R, G and B represent brightness values of red color, green color and blue color respectively.

In 3), the Hash fingerprints of the images are obtained by difference Hashing (dHash).

In 5), the overlapping rate of the current colonoscopy image with any one of the n previous colonoscopy images is calculated by the following equation:

$$Sim = \frac{100 \times (64 - d(x, y))}{64},$$

where d(x, y) represents the Hamming distance between different images, d(x, y)=Σx⊕y, x and y represent character strings corresponding to different images, respectively, referring to the Hash fingerprints of the images, and ⊕ represents exclusive OR.

In 7), the weighted overlapping rate at the point in time t is converted into a stability coefficient by the following equation: ESim=100−$\overline{Sim}$, where $\overline{Sim}$ represents the weighted similarity of the images at the point in time t.

The disclosure further provides a device for monitoring a colonoscope withdrawal speed. The device comprises an acquisition module, a calculation module and a display module. The acquisition module comprises video signal acquisition equipment, which is responsible for real-time acquisition of video signal from a digestive endoscopy equipment. The calculation module comprises a computer. The video signal is transmitted to the computer for real-time calculation and monitoring of the colonoscopy withdrawal speed. The display module is responsible for real-time display of endoscopic video image, current colonoscopy withdrawal speed and prompt information to doctors.

Specifically, the device comprises:

an image acquisition module configured to acquire, by endoscopic equipment, a real-time video of colonoscopy, decode the video into images, crop the images, and zoom-out the cropped images where the texture information of the images is retained;

a grayscale image conversion module configured to convert the images comprising the texture information to grayscale images;

a Hash fingerprint acquisition module configured to obtain the Hash fingerprints of the images;

a Hamming distance calculation module configured to calculate the Hamming distance between different images;

a similarity calculation module configured to compare the Hash fingerprints of a current colonoscopy image with n previous colonoscopy images, to obtain an overlapping rate of the current colonoscopy image with any one of the n previous colonoscopy images, thereby obtaining a similarity between the current colonoscopy image and the any one of the n previous colonoscopy images;

a weighted similarity calculation module configured to calculate the weighted similarity of the images at a point in time t;

a stability coefficient conversion module configured to convert the weighted overlapping rate at the point in time t into a stability coefficient;

a mean stability coefficient conversion module configured to calculate a mean stability coefficient of the colonoscopy images within a period of time 0-t;

a colonoscopy video analysis module configured to analyze the real-time video of colonoscopy to obtain a first boundary between a standard colonoscopy video and a sub-standard colonoscopy video and a second boundary between the sub-standard colonoscopy video and a low-quality colonoscopy video, respectively; and a withdrawal speed feedback module configured to monitor in real time a stability coefficient of a withdrawal by a physician performing the colonoscopy, and feed the stability coefficient to the physician, wherein: when the stability coefficient is less than the first boundary, indicating the withdrawal speed of the colonoscopy is within a normal range; when the stability coefficient is greater than the first boundary, indicating the withdrawal speed of the colonoscopy is not within the normal range; when the stability coefficient is between the first boundary and the second boundary, a warning signal is given; and when the stability coefficient is greater than the second boundary, an emergency alarm is given.

Further, in the similarity calculation module, the overlapping rate of the current colonoscopy image with any one of the n previous colonoscopy images is calculated by the following equation:

$$Sim = \frac{100 \times (64 - d(x, y))}{64},$$

where d(x, y) represents the Hamming distance between different images, d(x, y)=Σx⊕y, x and y represent character strings corresponding to different images, respectively, referring to the Hash fingerprints of the images, and ⊕ represents exclusive OR Further, in the stability coefficient conversion module, the weighted overlapping rate at the point in time t is converted into a stability coefficient by the following equation: $ESim = 100 - \overline{Sim}$, where $\overline{Sim}$ represents the weighted similarity of the images at the point in time t.

The following advantages are associated with the method and device for monitoring a colonoscope withdrawal speed: by analyzing the stability of colonoscopy images at an instantaneous moment or within a period of time, the colonoscope withdrawal speed is reflected in real time to remind doctors to control the withdrawal speed within the safe range during colonoscopy, thus improving the effectiveness of colonoscopy.

BRIEF DESCRIPTION OF THE DRAWINGS

FIG. 3 is a schematic view of a closest mapping point, in the original image, of a pixel (x, y) in a target interpolated graph.

DETAILED DESCRIPTION

To further illustrate the invention, embodiments detailing a method and device for monitoring a colonoscope withdrawal speed are described below. It should be noted that the following embodiments are intended to describe and not to limit the disclosure.

Figure 1:
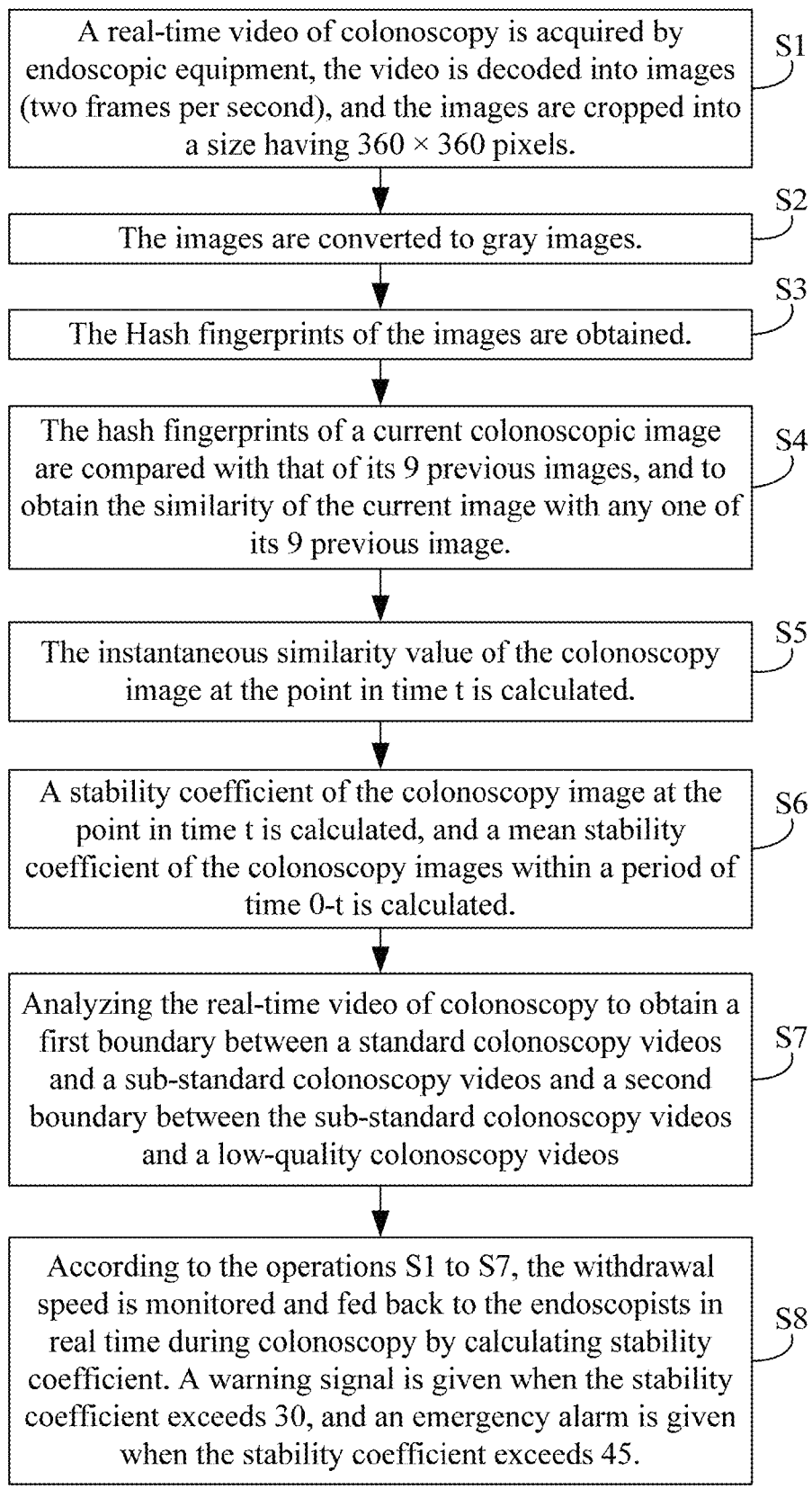
FIG. 1 is a flowchart of a method for monitoring a colonoscope withdrawal speed according to one embodiment of the disclosure.

Referring to FIG. 1, the disclosure provides a method for monitoring a colonoscope withdrawal speed, which is detailed as follows.

S1: A real-time video of colonoscopy is acquired by endoscopic equipment, the video is decoded into images (two frames per second), the images are cropped into a size having 360×360 pixels, and the cropped images are further zoomed-out wherein texture information of the images is retained.

A 360×360 image has more than 100,000 pixels and contains a huge amount of information and lots of details. Therefore, it is necessary to zoom out the image to remove the unnecessary details of the images, leave only basic information such as structure, brightness and darkness, and discard the differences in images caused by different sizes and proportions.

Figure 2:
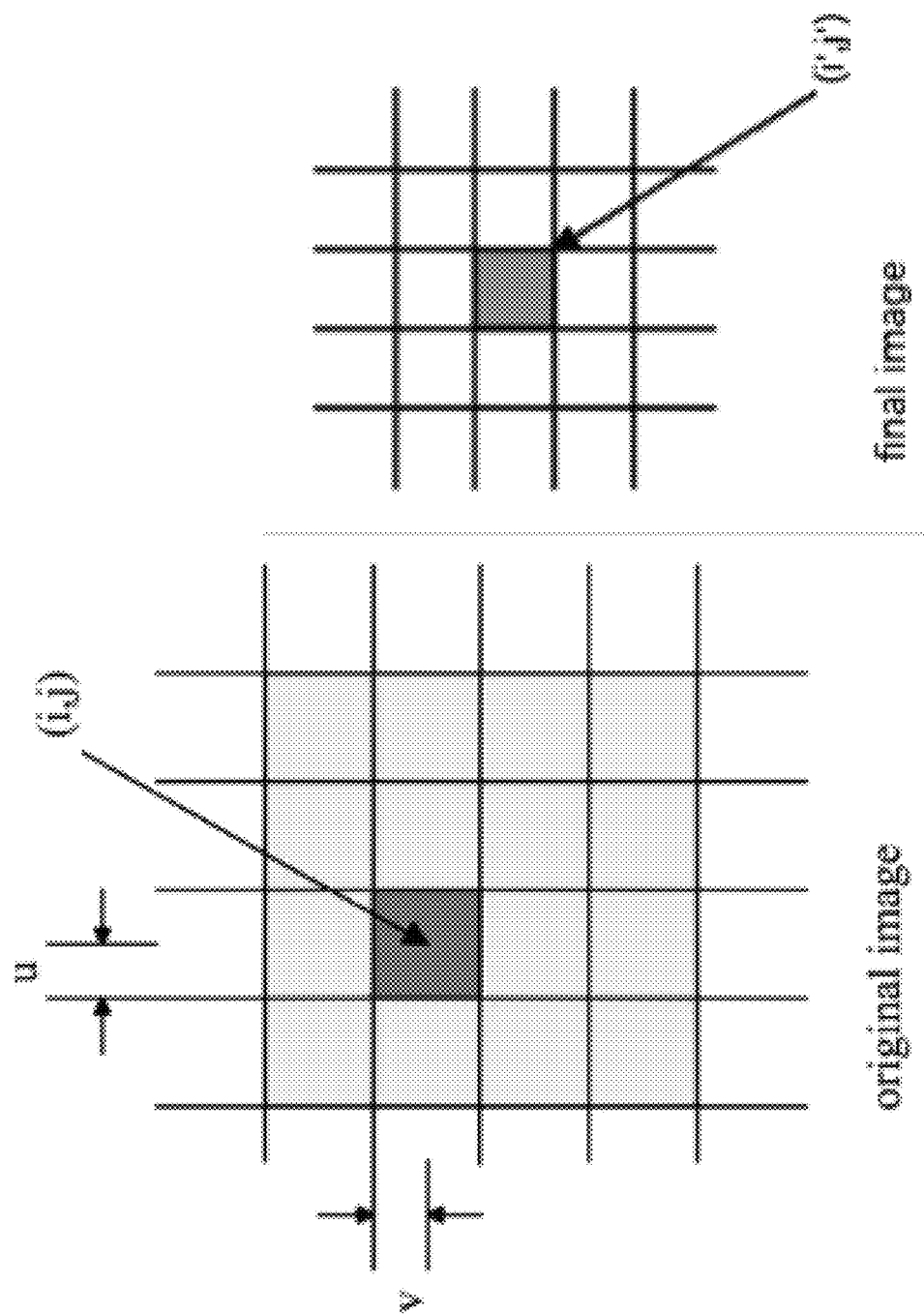
FIG. 2 shows the principle of zooming-out images by bicubic interpolation.

The images are zoomed-out by bicubic (cubic convolution) interpolation. The zoomed-out images are high in quality and less distorted, in spite of heavy calculation burden. As shown in FIG. 2 and the mathematical expression for bicubic interpolation that, the pixel value corresponding to the coordinate (i', j') in the zoomed-out image after interpolation is the convolution sum of weights of 16 pixels adjacent to the coordinate (i, j) in the original image. P00 in FIG. 3 represents the closest mapping point, in the original image, of a pixel (x, y) in a target interpolated graph. Let the expression of the pixel value of each coordinate (i, j) in the original image be f(i, j), then the pixel value of the corresponding coordinate after interpolation is F(i', j'), which can be obtained by the following equation:

$$F(i',j') = \Sigma_{row=-1}^{2} \Sigma_{col=-1}^{2} f(i+\text{row}, j+\text{col}) S(\text{row}-v) S(\text{col}-u) \quad (1),$$

where v represents the deviation of the number of rows and u represents the deviation of the number of columns; row represents a certain row and col represents a certain column; S(x) represents the interpolation expression which may be selected according to actual requirements, commonly including triangle interpolation, Bell interpolation and B spline interpolation. In this embodiment of the disclosure, Bell interpolation is used.

To calculate the dHash value of the images better, in this embodiment of the disclosure, the images are zoomed-out to a size having 9×8 pixels, i.e., total 72 pixels.

S2: The images are converted to grayscale images. Usually, if the similarity of the contrast images is less related to color, the images are converted to grayscale images to decrease the complexity in the subsequent calculations. Weighted averaging is used: since people have different sensitivities to red light, green light and blue light, a different weight is provided for each pixel in the images to obtain the gray value of this pixel:

$$\text{Gray}=0.30\times R+0.59\times G+0.11\times B \quad (2).$$

S3: The Hash fingerprints of the images are obtained. That is, the Hash strings corresponding to the images are obtained. The common perceptual hash algorithms include aHash, pHash and dHash. aHash (average hashing) is fast, but often low in accuracy; pHash (perception hashing) is high in accuracy, but relatively slow; and dHash (difference hashing) is high in accuracy and also fast. Therefore, in this embodiment of the disclosure, the Hash fingerprints of the images are obtained by dHash.

S4: The Hamming distance between different images is calculated. In the information theory, the Hamming distance represents the number of different characters in the corresponding position of two equal-length strings. The Hamming distance between the strings x and y is denoted by d(x, y):

$$d(x,y)=\Sigma x \oplus y \quad (3)$$

where $\oplus$ represents exclusive OR. From another prospective, the Hamming distance measures the minimum number of replacements needed to change the string x to the character string y by means of character replacement. The Hamming distance indicates how many steps are needed to change A to B. For example, for strings "abc" and "ab3", the Hamming distance is 1, since it is just needed to change "c" to "3".

The Hamming distance in dHash is the number of differences to be changed. The differences are denoted by 0 and 1, which can be considered as binary. For binary 0110 and 1111, the Hamming distance is 2. The dHash values of the two images are converted to binary differences which are then subject to exclusive OR. The number of "1" in the result of the exclusive OR operation, i.e., the number of different digits, is counted. It is the Hamming distance.

S5: The Hash fingerprints of a current colonoscopy image with the Hash fingerprints of 9 previous colonoscopy images are compared, to obtain an overlapping rate of the current image with any one of the 9 images, i.e., the similarity between the current colonoscopy image and any one of the 9 images:

$$Sim = \frac{100 \times (64 - d(x, y))}{64}.$$

S6: The weighted similarity of the images at a point in time t is calculated:

$$\overline{Sim} = \Sigma_{i=1}^{9} \frac{i}{45} \times Sim_i,$$

where $Sim_i$ represents the similarity between the current image and the $i^{th}$ image (i ranges from 1 to 9) before the current image at the point in time t.

S7: The weighted overlapping rate at the point in time t is converted into a stability coefficient: $ESim=100-\overline{Sim}$.

S8: A mean stability coefficient of the colonoscopy images within a period of time 0-t is calculated, wherein the mean stability coefficient is the mean of stability coefficients at all points in time.

S9: 50 standard colonoscopy videos with a withdrawal time of more than 6 minutes, 50 sub-standard colonoscopy videos with a withdrawal time of 4-6 minutes, and 50 low-quality colonoscopy videos with a withdrawal time of less than 4 minutes are analyzed to obtain the following result:

$$\text{level} = \begin{cases} A, \overline{ESim} \leq 30 \\ B, 30 < \overline{ESim} < 45 \\ C, \overline{ESim} \geq 45 \end{cases}.$$

S10: According to the operations S1 to S8, the stability coefficient of the withdrawal by a physician performing the colonoscopy is monitored in real time and fed back to the physician, a warning signal is given when the withdrawal speed exceeds 30, and an emergency alarm is given when the withdrawal speed exceeds 45.

The disclosure further provides a device for monitoring a colonoscope withdrawal speed, the device comprising:
- an image acquisition module, configured to acquire, by endoscopic equipment, a real-time video of colonoscopy, decode the video into images, crop the images, and zoom out the cropped images where the texture information of the images is retained;
- a grayscale image conversion module, configured to convert the images comprising the texture information to grayscale images;
- a Hash fingerprint acquisition module, configured to obtain the Hash fingerprints of the images;
- a Hamming distance calculation module, configured to calculate the Hamming distance between different images;
- a similarity calculation module, configured to compare the Hash fingerprints of a current colonoscopy image with n previous colonoscopy images, to obtain an overlapping rate of the current colonoscopy image with any one of the n previous colonoscopy images, thereby obtaining a similarity between the current colonoscopy image and the any one of the n previous colonoscopy images;
- a weighted similarity calculation module, configured to calculate a weighted similarity of the images at a point in time t;
- a stability coefficient conversion module, configured to convert the weighted overlapping rate at the point in time t into a stability coefficient;
- a mean stability coefficient conversion module, configured to calculate a mean stability coefficient of the colonoscopy images within a period of time 0-t;
- a colonoscopy video analysis module, configured to analyze the real-time video of colonoscopy to obtain a first boundary between a standard colonoscopy video and a sub-standard colonoscopy video and a second boundary between the sub-standard colonoscopy video and a low-quality colonoscopy video, respectively; and a withdrawal speed feedback module, configured to monitor in real time a stability coefficient of a withdrawal by a physician performing the colonoscopy, and feed the stability coefficient to the physician, wherein: when the stability coefficient is less than the first boundary, indicating the withdrawal speed of the colonoscopy is within a normal range; when the stability coefficient is greater than the first boundary, indicating the withdrawal speed of the colonoscopy is not within the normal range; when the stability coefficient is between the first boundary and the second boundary, a warning signal is given; and when the stability coefficient is greater than the second boundary, an emergency alarm is given.

It will be obvious to those skilled in the art that changes and modifications may be made, and therefore, the aim in the appended claims is to cover all such changes and modifications.

What is claimed is:

1. A method, comprising:
   1) acquiring, by endoscopic equipment, a real-time video of colonoscopy; decoding the video into images, cropping the images, and zooming-out the cropped images to remove the color and leave texture information of the images;
   2) converting the images comprising the texture information to grayscale images;
   3) obtaining Hash fingerprints of the grayscale images;
   4) calculating a Hamming distance between the images;
   5) comparing the Hash fingerprints of a current colonoscopy image with n previous colonoscopy images where n is a number, to obtain an overlapping rate of the current colonoscopy image with any one of the n previous colonoscopy images, thereby obtaining a similarity between the current colonoscopy image and the any one of the n previous colonoscopy images;
   6) calculating a weighted similarity of the images at a point in time t, wherein the weighted similarity refers to a weighted average value of similarity between a current image and its previous 9 frames, thereby acquiring a representative value of the similarity within the point in time t, and the closer two frames are, the higher the weighted similarity is;
   7) converting the weighted similarity of the images at the point in time t into a stability coefficient;
   8) calculating a mean stability coefficient of colonoscopy images within a period of time 0-t as follows: the mean stability coefficient=100−weighted similarity, time 0 is a timepoint where the colonoscopy withdrawal process begins, and the time t is any given timepoint;
   9) analyzing the real-time video of colonoscopy to obtain a first boundary between a standard colonoscopy video where a withdrawal time exceeds 6 min and a sub-standard colonoscopy video where a withdrawal time is between 5-6 min and a second boundary between the sub-standard colonoscopy video and a low-quality colonoscopy video where a withdrawal time is less than 5 min, respectively; and
   10) monitoring in real time, according to the operations 1) to 8), a stability coefficient of a withdrawal process, and feeding back the stability coefficient to an operator, wherein: when the stability coefficient is less than the first boundary, indicating the withdrawal speed of the colonoscopy is within a normal range and the withdrawal speed meets the requirement of standard colonoscopy guideline; when the stability coefficient is greater than the first boundary, indicating the withdrawal speed of the colonoscopy is not within the normal range; when the stability coefficient is between the first boundary and the second boundary, a warning signal is presented in a dashboard monitoring real-time withdrawal speed during colonoscopy; and when the stability coefficient is greater than the second boundary, an emergency alarm is given.

2. The method of claim 1, wherein in 1), the cropped images are zoomed-out by bicubic interpolation.

3. The method of claim 1, wherein in 2), the images are converted to the grayscale images by the following equation: Gray=0.30×R+0.59×G+0.11×B; where R, G and B represent brightness values of red color, green color and blue color, respectively.

4. The method of claim 1, wherein in 3), the Hash fingerprints of the images are obtained by difference Hashing (dHash).

5. The method of claim 1, wherein in 5), the overlapping rate of the current colonoscopy image with any one of the n previous colonoscopy images is calculated by the following equation:

$$Sim = \frac{100 \times (64 - d(x, y))}{64},$$

where d(x, y) represents the Hamming distance between different images, $d(x, y)=\Sigma x \oplus y$, x and y represent character strings corresponding to different images, respectively, referring to the Hash fingerprints of the images, and $\oplus$ represents exclusive OR.

6. The method of claim 1, wherein in 7), the weighted overlapping rate at the point in time t is converted into the stability coefficient by the following equation: ESim=100−$\overline{Sim}$, where $\overline{Sim}$ represents the weighted similarity of the images at the point in time t.

7. A device, comprising:
   an image acquisition module, configured to acquire, by endoscopic equipment, a real-time video of colonoscopy, decode the video into images, crop the images, and zoom-out the cropped images wherein texture information of the images is retained;
   a grayscale image conversion module, configured to convert the images comprising the texture information to grayscale images;
   a Hash fingerprint acquisition module, configured to obtain Hash fingerprints of the images;
   a Hamming distance calculation module, configured to calculate a Hamming distance between different images;
   a similarity calculation module, configured to compare the Hash fingerprints of a current colonoscopy image with n previous colonoscopy images, to obtain an overlapping rate of the current colonoscopy image with any one of the n previous colonoscopy images, thereby obtaining a similarity between the current colonoscopy image and the any one of the n previous colonoscopy images;
   a weighted similarity calculation module, configured to calculate a weighted similarity of the images at a point in time t;

a stability coefficient conversion module, configured to convert the weighted overlapping rate at the point in time t into a stability coefficient;

a mean stability coefficient conversion module, configured to calculate a mean stability coefficient of colonoscopy images within a period of time 0-t;

a colonoscopy video analysis module, configured to analyze the real-time video of colonoscopy to obtain a first boundary between a standard colonoscopy video and a sub-standard colonoscopy video and a second boundary between the sub-standard colonoscopy video and a low-quality colonoscopy video, respectively; and a withdrawal speed feedback module, configured to monitor in real time a stability coefficient of a withdrawal by a physician performing the colonoscopy, and feed the stability coefficient to the physician, wherein: when the stability coefficient is less than the first boundary, indicating the withdrawal speed of the colonoscopy is within a normal range; when the stability coefficient is greater than the first boundary, indicating the withdrawal speed of the colonoscopy is not within the normal range; when the stability coefficient is between the first boundary and the second boundary, a warning signal is given; and when the stability coefficient is greater than the second boundary, an emergency alarm is given.

8. The device of claim 7, wherein in the similarity calculation module, the overlapping rate of the current colonoscopy image with any one of the n previous colonoscopy images is calculated by the following equation:

$$Sim = \frac{100 \times (64 - d(x, y))}{64},$$

where $d(x, y)$ represents the Hamming distance between different images, $d(x, y) = \Sigma x \oplus y$, x and y represent character strings corresponding to different images, respectively, referring to the Hash fingerprints of the images, and $\oplus$ represents exclusive OR.

9. The device of claim 7, wherein in the stability coefficient conversion module, the weighted overlapping rate at the point in time t is converted into the stability coefficient by the following equation: $ESim = 100 - \overline{Sim}$, where $\overline{Sim}$ represents the weighted similarity of the images at the point in time t.

* * * * *